(12) United States Patent
Shibamoto

(10) Patent No.: US 9,242,921 B2
(45) Date of Patent: Jan. 26, 2016

(54) PROCESS FOR PRODUCING AROMATIC CARBOXYLIC ACID

(75) Inventor: Akihiro Shibamoto, Himeji (JP)

(73) Assignee: DAICEL CHEMICAL INDUSTRIES, LTD., Osaka-Shi (JP)

( * ) Notice: Subject to any disclaimer, the term of this patent is extended or adjusted under 35 U.S.C. 154(b) by 615 days.

(21) Appl. No.: 12/992,658

(22) PCT Filed: May 21, 2009

(86) PCT No.: PCT/JP2009/059366
§ 371 (c)(1),
(2), (4) Date: Nov. 15, 2010

(87) PCT Pub. No.: WO2009/142269
PCT Pub. Date: Nov. 26, 2009

(65) Prior Publication Data
US 2011/0071313 A1    Mar. 24, 2011

(30) Foreign Application Priority Data

May 23, 2008    (JP) .................................. 2008-135844

(51) Int. Cl.
*C07C 51/265*    (2006.01)
(52) U.S. Cl.
CPC .................................... *C07C 51/265* (2013.01)
(58) Field of Classification Search
None
See application file for complete search history.

(56) References Cited

U.S. PATENT DOCUMENTS

| | | | |
|---|---|---|---|
| 5,041,633 | A | 8/1991 | Partenheimer et al. |
| 2007/0191634 | A1 | 8/2007 | Hirai et al. |
| 2008/0269507 | A1 | 10/2008 | Kajikawa et al. |

FOREIGN PATENT DOCUMENTS

| | | |
|---|---|---|
| EP | 0375812 A1 | 7/1990 |
| EP | 1 164 131 A1 | 12/2001 |
| JP | 2-184652 A | 7/1990 |
| JP | 2001-354596 A | 12/2001 |
| JP | 2002-308805 A | 10/2002 |
| JP | 2002-331242 A | 11/2002 |
| JP | 2005-298380 A | 10/2005 |
| JP | 2006-273793 A | 10/2006 |
| WO | WO 02/40154 A1 | 5/2002 |
| WO | WO 2006/095568 A1 | 9/2006 |

OTHER PUBLICATIONS

Hirai et al., JP2006-273793 English Machine Translation.*
"International Search Report", dated, Jul. 21, 2009, issued in PCT/JP2009/059366.
CSJ: The Chemical Society of Japan Koen Yokoshu, The 74th Spring Meeting, Mar. 27-30, 1998, vol. 74th, No. 2, p. 1011.
Ishii et al., "Alkane Oxidation with Molecular Oxygen Using a New Efficient Catalytic System: N-Hydroxyphthalimide (NHPI) Combined with Co(acac)n (n=2 or 3)", J. Org. Chem, 1996, vol. 61, No. 14, pp. 4520-4526.
Tashiro et al., "A New Strategy for the Preparation of Terephthalic Acid by the Aerobic Oxidation of p-Xylene Using N-Hydroxyphthalimide as a Catalyst", Adv. Synth. Catal., 2001, 343, No. 2, pp. 220-225.
International Preliminary Report on Patentability (Forms PCT/IB/373, PCT/ISA/237 AND PCT/ISA/210) in International Application No. PCT/JP2009/060629 mailed Jan. 11, 2011.

* cited by examiner

*Primary Examiner* — Rosalynd Keys
*Assistant Examiner* — Jennifer C Sawyer
(74) *Attorney, Agent, or Firm* — Birch, Stewart, Kolasch & Birch, LLP

(57) ABSTRACT

A process for allowing an oxidation reaction efficiently to produce an object aromatic carboxylic acid with an efficient productivity by improving a catalyst activity even in the presence of a relatively small amount of a catalyst is provided.
The process comprises oxygen-oxidizing an aromatic compound having an alkyl group and/or an alkylene group as a substrate in the presence of a catalyst containing a cyclic imino unit having an N—OR group (wherein R represents a hydrogen atom or a protecting group for a hydroxyl group) and a transition metal co-catalyst (a cobalt compound, a manganese compound, and a zirconium compound) to produce the aromatic carboxylic acid corresponding to the aromatic compound. The oxidation reaction is carried out with feeding a mixture of the catalyst and at least one member selected from the group consisting of the substrate, a reaction intermediate (e.g., a ketone and an aldehyde), and a reaction product (e.g., water and an aromatic carboxylic acid) successively or continuously to the oxidation reaction system. The oxidation reaction may usually be carried out in the absence of a reaction solvent. The reaction may be conducted with removing water produced by the reaction from the reaction system.

8 Claims, No Drawings

PROCESS FOR PRODUCING AROMATIC CARBOXYLIC ACID

TECHNICAL FIELD

The present invention relates to a process for producing an aromatic carboxylic acid, and the process is useful for obtaining an aromatic carboxylic acid by oxidizing an aromatic compound (e.g., an arene compound) having an alkyl group and/or an alkylene group with molecular oxygen in a system having a small amount of a reaction solvent such as an organic solvent (particularly, in the absence of a reaction solvent).

BACKGROUND ART

An aromatic carboxylic acid or a derivative thereof (for example, an ester of an aromatic carboxylic acid, and an aromatic carboxylic anhydride) is used as a raw material for various resins and is in great demand all over the world. For example, terephthalic acid, which is derived from p-xylene, has been used as a raw material for a general-purpose polyethylene terephthalate) (PET) resin all over the world. Moreover, pyromellitic anhydride, which is derived from durene, has been widely used for various purposes such as an electronic material.

Currently, most of the aromatic carboxylic acids or derivatives thereof are produced by oxygen-oxidizing (or aerobically oxidizing) a corresponding aromatic compound. For example, a carboxylic acid (e.g., terephthalic acid) is produced by an air oxidation method using a catalyst system containing a transition metal salt and bromine. Such a method, however, has some problems, for example, the necessity of a relatively high reaction temperature or the corrosion of an apparatus by a halogen-containing catalyst.

Thus a method for carrying out a relatively efficient reaction under a relatively mild condition has been examined. For example, Japanese Patent Application Laid-Open No. 354596/2001 (JP-2001-354596A, Patent Document 1) discloses that, for producing an organic compound using an imide catalyst, a successive addition of the imide catalyst to a reaction system improves the conversion of a substrate and/or the selectivity of an object compound. However, this process is basically conducted on the premise that the reaction is carried out in the presence of a solvent, and the purification efficiency is low. Moreover, Japanese Patent Application Laid-Open No. 331242/2002 (JP-2002-331242A, Patent Document 2) discloses that use of a highly fat-soluble imide catalyst allows efficient oxidation of cyclohexane or the like in the absence of a solvent or even in a reaction solvent having a small polarity. However, there still remains an insufficient catalyst activity or an insufficient yield of the product for such conventional processes. In addition, there is much room for an effort for a reduction in the cost. Therefore, the production process is required to produce the object compound at a high selectivity and a high yield by allowing the reaction to proceed efficiently in the presence of a relatively small amount of a catalyst, and to have an improved purification efficiency.

RELATED ART DOCUMENTS

Patent Documents

[Patent Document 1] JP-2001-354596A (Claim 1 and paragraph number [0007])
[Patent Document 2] JP-2002-331242A (Claim 1 and paragraph number [0011])

SUMMARY OF THE INVENTION

Problems to be Solved by the Invention

It is therefore an object of the present invention to provide a process for producing an object aromatic carboxylic acid efficiently by improving a catalyst activity.

It is another object of the invention to provide a process for allowing an oxidation reaction to proceed efficiently even in the presence of a relatively small amount of a catalyst to produce an aromatic carboxylic acid with a high purification efficiency and an efficient productivity.

Means to Solve the Problems

The inventors of the present invention made intensive studies to achieve the above objects and finally found that (i) an aromatic compound having an alkyl group and/or an alkylene group is oxidized using a specific imide catalyst and a transition metal co-catalyst in the absence of a solvent or in the presence of a small amount of a solvent to produce an aromatic carboxylic acid, the resulting aromatic carboxylic acid forms a salt with the transition metal co-catalyst, and the salt probably serves as an active species (or an activated species) to allow the oxidation reaction to proceed efficiently, and that (ii) the production process provides a high purification efficiency and is advantageous in terms of energy, because it is unnecessary to eliminate a large amount of a solvent component. Moreover, the inventors found that (iii) the oxidation reaction can be accelerated by feeding an imide catalyst to the reaction system successively or continuously together with the substrate, a reaction intermediate thereof and/or a reaction product thereof, that (iv) the oxidation reaction proceeds efficiently even at a small amount of a catalyst since an imide radical (>N—O.) is appropriately dispersed in such a reaction system to participate in the reaction efficiently, and that (v) the oxidation reaction carried out without using the imide catalyst produces a by-product compound by decarboxylation of the aromatic compound as the substrate, while addition of an imide catalyst decreases the production of the by-product. The present invention was accomplished based on the above findings.

That is, the present invention includes a process for producing an aromatic carboxylic acid, which comprises oxygen-oxidizing an aromatic compound having an alkyl group and/or an alkylene group as a substrate (or oxidizing an aromatic compound having an alkyl group and/or an alkylene group as a substrate with oxygen) in the presence of a catalyst and a transition metal co-catalyst to produce the aromatic carboxylic acid corresponding to the aromatic compound, wherein the catalyst comprises a nitrogen atom-containing cyclic compound containing a skeleton represented by the following formula (1) as a constituent element of the cyclic ring (hereinafter, the catalyst may simply be referred to as a catalyst having a cyclic imino unit, an imide compound or a catalyst). The oxidation reaction is carried out with feeding a mixture of the catalyst and at least one member selected from the group consisting of the substrate, and a reaction intermediate obtainable by the oxidation reaction of the substrate (or a reaction intermediate corresponding to a compound obtained by the oxidation reaction of the substrate), and a reaction product obtainable by the oxidation reaction of the substrate (or a reaction product corresponding to a compound obtained by the oxidation reaction of the substrate) successively or continuously to the oxidation reaction system.

[Formula 1]

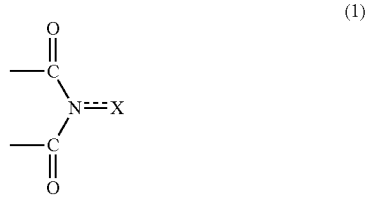

(1)

In the formula, X represents an oxygen atom or an —OR group (wherein R represents a hydrogen atom or a protecting group for a hydroxyl group), and a double line consisting of a solid line and a broken line and connecting "N" and "X" represents a single bond or a double bond.

The oxidation reaction is usually carried out in the absence of a reaction solvent (which does not contain the substrate, the reaction intermediate and the reaction product). In the production process, the reaction may be carried out with removing water produced (or obtained) by the reaction from the reaction system.

As a component to be fed to the reaction system together with the catalyst having a cyclic imino unit, the following may be used: at least one member selected from the group consisting of (b-1) an aromatic compound having an alkyl group and/or an alkylene group as the substrate, (b-2) a carbonyl compound corresponding to the aromatic compound as the substrate [for example, a reaction intermediate (e.g., a ketone and an aldehyde) and a reaction product (e.g., an aromatic carboxylic acid)], and (b-3) water as the reaction product, and the like. The catalyst having the cyclic imino unit may be a water-soluble or water-dispersive imide compound. The substrate may comprise an aromatic compound having one or two $C_{1-4}$alkyl and/or $C_{1-4}$alkylene substituent(s) on an aromatic ring thereof. Moreover, the aromatic carboxylic acid produced by the oxidation reaction may be capable of forming a salt with the transition metal co-catalyst. The catalyst having the cyclic imino unit may be at least one member selected from the group consisting of an alkanedicarboximide, an alkenecarboximide, and an isocyanuric acid having an oxygen atom or an —OR group (wherein R has the same meaning as defined above) on at least one nitrogen atom thereof. The transition metal co-catalyst may at least contain a metal component of the Group 9 of the Periodic Table of Elements and a metal component of the Group 7 of the Periodic Table of Elements. The transition metal co-catalyst may contain a cobalt compound and a manganese compound.

Incidentally, hereinafter the term "aromatic carboxylic acid" means not only a carboxylic acid having a free carboxyl group but also a derivative of an aromatic carboxylic acid, for example, a compound having an acid anhydride group, an ester of a carboxylic acid [e.g., a lower alkyl ester (e.g., a $C_{1-4}$alkyl ester) such as a methyl ester or an ethyl ester], and the like.

Moreover, the "reaction solvent", the "organic solvent" and the "solvent" do not contain the substrate, the reaction intermediate and the reaction product and thus mean a component different from the substrate, the reaction intermediate and the reaction product. Accordingly, the term "substrate, reaction intermediate and reaction product" may serve as a medium in the reaction system.

Effects of the Invention

According to the present invention, since the imide catalyst is fed to the reaction system successively or continuously together with the substrate, the reaction intermediate and/or the reaction product, the catalyst activity is improved to produce an object aromatic carboxylic acid efficiently. Therefore, the oxidation reaction allows to proceed efficiently even at a relatively small amount of the catalyst. Further, since, in the oxidation reaction, a reaction solvent as usually employed for oxidation reaction (for example, an organic solvent which is different from the substrate, the reaction intermediate and the reaction product) is not used or there is just a small amount of the reaction solvent in a case where the reaction solvent is used, the aromatic carboxylic acid can be obtained with an improved purification efficiency and an efficient productivity.

DESCRIPTION OF EMBODIMENTS

According to the present invention, a process for producing an aromatic carboxylic acid comprises oxygen-oxidizing an aromatic compound having an alkyl group and/or an alkylene group as a substrate in the presence of a catalyst containing a cyclic imino unit having a skeleton represented by the above-mentioned formula (1) and a transition metal co-catalyst to give the aromatic carboxylic acid corresponding to the aromatic compound. The oxidation reaction is carried out while feeding a mixture of the catalyst and at least one member selected from the group consisting of the substrate, a reaction intermediate and a reaction product to the oxidation reaction system successively or continuously.

(Catalyst Having Cyclic Imino Unit)

The imide compound has a cyclic imino unit containing a skeleton represented by the above-mentioned formula (1) (skeleton (1)) as a constituent element of a ring thereof. It is sufficient that the imide compound has at least one skeleton (1) in a molecule thereof, and the imide compound may have a plurality of skeletons (1). Moreover, the cyclic imino unit may form one ring by a plurality of skeletons (1) as a constituent element. The cyclic imino unit may have one or a plurality of hetero atom(s) (for example, a nitrogen atom, a sulfur atom, and an oxygen atom (particularly, a nitrogen atom)) other than a nitrogen atom of the skeleton (1), as a constituent atom of a ring thereof.

In the skeleton (1) [or the cyclic imino unit of the catalyst (imide compound)], X represents an oxygen atom, an —OH group, or a hydroxyl group protected by a protecting group R. The protecting group may be referred to, for example, Japanese Patent Application Laid-Open No. 308805/2002 (JP-2002-308805A, Patent Document 3), Japanese Patent Application Laid-Open No. 273793/2006 (JP-2006-273793A, Patent Document 4), and WO 2002/040154 (Patent Document 5). The protecting group R may include, for example, a hydrocarbon group which may have a substituent [for example, an alkyl group, an alkenyl group (e.g., allyl group), a cycloalkyl group, an aryl group which may have a substituent, and an aralkyl group which may have a substituent]; a group which can form an acetal or hemiacetal group with a hydroxyl group, for example, a $C_{1-3}$alkyl group having a substituent [e.g., a halo$C_{1-2}$alkyl group (e.g., 2,2,2-trichloroethyl group), a $C_{1-4}$alkoxy$C_{1-2}$alkyl group (e.g., methoxymethyl group, ethoxymethyl group, isopropoxymethyl group, 2-methoxyethyl group, 1-ethoxyethyl group, and 1-isopropoxyethyl group), a $C_{1-4}$alkylthio$C_{1-2}$alkyl group corresponding to such a $C_{1-4}$alkoxy$C_{1-2}$alkyl group, a halo$C_{1-4}$alkoxy$C_{1-2}$alkyl group (e.g., 2,2,2-trichloroethoxymethyl group, and bis(2-chloroethoxy)methyl group), a $C_{1-4}$alkyl$C_{1-4}$alkoxy$C_{1-2}$alkyl group (e.g., 1-methyl-1-methoxyethyl group), a $C_{1-4}$alkoxy$C_{1-3}$alkoxy$C_{1-2}$alkyl group (e.g., 2-methoxyethoxymethyl group), a $C_{1-4}$alkylsilyl$C_{1-4}$alkoxy$C_{1-2}$alkyl group (e.g., 2-(trimethylsilyl)ethoxymethyl group), and an aralkyloxy$C_{1-2}$alkyl group (e.g., benzyloxymethyl group)], a 5- or 6-membered heterocycle group having a hetero atom selected from the group consisting of a nitrogen atom, an oxygen atom and a sulfur atom (e.g., a saturated heterocycle group such as tetrahydropyranyl group or tetrahydrofuranyl group), and a 1-hydroxy-$C_{1-20}$alkyl group which may have a substituent (e.g., a 1-hydroxy-$C_{1-10}$alkyl group such as 1-hydroxyethyl or 1-hydroxyhexyl group, and 1-hydroxy-1-phenylmethyl group); an acyl group (for example, a saturated or unsaturated alkylcarbonyl group, e.g., a $C_{1-20}$alkyl-carbonyl group such as formyl, acetyl, propionyl, butyryl, or isobutyryl group; acetoacetyl group; an alicyclic acyl group, e.g., a $C_{4-10}$cycloalkyl-carbonyl group such as cyclopentanecarbonyl or cyclohexanecarbonyl group; and a $C_{6-12}$aryl-carbonyl group such as benzoyl or naphthoyl group), a sulfonyl group having an alkyl group which may be halogenated (e.g., an alkylsulfonyl group such as methanesulfonyl group or trifluoromethanesulfonyl group, and an arylsulfonyl group such as benzenesulfonyl, p-toluenesulfonyl, or naphthalenesulfonyl group); an alkoxycarbonyl group (e.g., a $C_{1-4}$alkoxy-carbonyl group such as methoxycarbonyl group or ethoxycarbonyl group), an aralkyloxycarbonyl group (e.g., benzyloxycarbonyl group, and p-methoxybenzyloxycarbonyl group); a carbamoyl group which has either a substituent or no substituent (or a substituted or non-substituted carbamoyl group) (e.g., carbamoyl group, a $C_{1-4}$alkylcarbamoyl group such as methylcarbamoyl group, and phenylcarbamoyl group); a residual group obtained by eliminating a hydroxyl group from an inorganic acid (e.g., sulfuric acid, nitric acid, phosphoric acid, and boric acid); a dialkylphosphanothioyl group, a diarylphosphanothioyl group; and a silyl group having a substituent (or a substituted silyl group) (e.g., trimethylsilyl, t-butyldimethylsilyl, tribenzylsilyl, and triphenylsilyl group).

The preferred R may include a protecting group other than an alkyl group (e.g., methyl group), for example, a hydrogen atom; a group capable of forming an acetal or hemiacetal group with a hydroxyl group; and a hydrolyzable protecting group, which can be eliminated by hydrolysis, for example, a residual group obtained by eliminating a hydroxyl group from an acid such as a carboxylic acid, a sulfonic acid, a carbonic acid, a carbamic acid, a sulfuric acid, a phosphoric acid, or a boric acid (e.g., an acyl group, a sulfonyl group, an alkoxycarbonyl group, and a carbamoyl group).

In the formula, the double line consisting of a solid line and a broken line and connecting the nitrogen atom "N" and "X" represents a single bond or a double bond.

The catalyst (imide compound) having the cyclic imino unit may include, for example, a compound having 5-membered or 6-membered cyclic unit containing the skeleton (1) as a constituent element of the ring thereof. Such a compound is known and may be referred to the above-mentioned Patent Documents 3 to 5, and others. The compound having the 5-membered cyclic unit may include, for example, a compound represented by the following formula (2). The compound having the 6-membered cyclic unit may include, for example, a compound represented by the following formula (3) or (4).

[Formula 2]

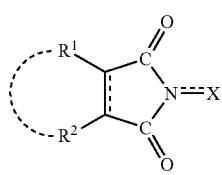

(2)

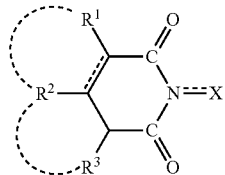

(3)

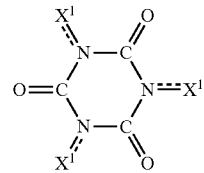

(4)

In the formulae, $R^1$, $R^2$ and $R^3$ are the same or different and each represent a hydrogen atom, a halogen atom, an alkyl group, an aryl group, a cycloalkyl group, a hydroxyl group, an alkoxy group, a carboxyl group, an oxycarbonyl group having a substituent (or a substituted oxycarbonyl group), an acyl group, or an acyloxy group, $R^1$ and $R^2$ may bond together to form an aromatic or non-aromatic ring with the adjacent carbon atoms, $R^2$ and $R^3$ may bond together to form an aromatic or non-aromatic ring with the adjacent carbon atoms. These rings may further have one or two cyclic imino units mentioned above. The double line consisting of a solid line and a broken line represents a single bond or a double bond. The group $X^1$ represents a hydrogen atom or X, and at least one of $X^1$ represents X. The group X has the same meaning as defined above.

The halogen atom represented by each of the substituents $R^1$, $R^2$ and $R^3$ may include an iodine atom, a bromine atom, a chlorine atom, and a fluorine atom. The alkyl group may include, for example, a straight chain or branched chain $C_{1-20}$alkyl group such as methyl, ethyl, propyl, isopropyl, butyl, isobutyl, s-butyl, t-butyl, hexyl, or decyl group (particularly, a $C_{1-16}$alkyl group). The cycloalkyl group may include a $C_{3-10}$cycloalkyl group such as cyclopentyl or cyclohexyl group. The aryl group may include phenyl group, naphthyl group, and others.

The alkoxy group may include, for example, a straight chain or branched chain $C_{1-20}$alkoxy group such as methoxy, ethoxy, isopropoxy, butoxy, t-butoxy, hexyloxy, octyloxy, decyloxy, dodecyloxy, tetradecyloxy, or octadecyloxy group (particularly, a $C_{1-16}$alkoxy group). The substituted oxycarbonyl group may include, for example, a $C_{1-20}$alkoxy-carbonyl group such as methoxycarbonyl, ethoxycarbonyl, isopropoxycarbonyl, butoxycarbonyl, t-butoxycarbonyl, hexyloxycarbonyl, octyloxycarbonyl, or decyloxycarbonyl group; a $C_{3-10}$cycloalkyloxy-carbonyl group such as cyclopentyloxycarbonyl or cyclohexyloxycarbonyl group; a $C_{6-12}$aryloxy-carbonyl group such as phenyloxycarbonyl or naphthyloxycarbonyl group; and a $C_{6-12}$aryl$C_{1-4}$alkyloxy-carbonyl group such as benzyloxycarbonyl group. The acyl group may include, for example, a $C_{1-20}$alkyl-carbonyl group such as formyl, acetyl, propionyl, butyryl, isobutyryl, valeryl, pivaloyl, hexanoyl, or octanoyl group; acetoacetyl group; a cycloalkylcarbonyl group such as cyclopentylcarbonyl or cyclohexylcarbonyl group (e.g., a $C_{3-10}$cycloalkyl-carbonyl group); and an aromatic acyl group such as benzoyl or naphthoyl group. The acyloxy group may include an acyloxy group corresponding to the acyl group, for example, a $C_{1-20}$alkyl-carbonyloxy group; acetoacetyloxy group; a cycloalkylcarbonyloxy group; and an arylcarbonyloxy group.

The substituents $R^1$, $R^2$ and $R^3$ may be the same or different from one another. Moreover, in the above-mentioned formulae (2) to (4), a broken line connecting $R^1$ with $R^2$ represents that $R^1$ and $R^2$ may bond together to form an aromatic or non-aromatic ring with the adjacent carbon atoms, and a broken line connecting $R^2$ with $R^3$ represents that $R^2$ and $R^3$ may bond together to form an aromatic or non-aromatic ring with the adjacent carbon atoms. Incidentally, the ring formed by bonding of $R^1$ and $R^2$ and the ring formed by bonding of $R^2$ and $R^3$ may be combined to form a polycyclic aromatic or non-aromatic condensed ring.

Each of the aromatic or non-aromatic ring formed by bonding of $R^1$ and $R^2$ and the aromatic or non-aromatic ring formed by bonding $R^2$ and $R^3$ may be, for example, an about 5- to 16-membered ring, preferably an about 6- to 14-membered ring, and more preferably an about 6- to 12-membered ring (e.g., an about 6- to 10-membered ring). Moreover, the aromatic or non-aromatic ring may be a heterocycle or a condensed heterocycle, and is practically a hydrocarbon ring or a hydrocarbon ring further having one or two cyclic imino units. Such a hydrocarbon ring may include, for example, a non-aromatic alicyclic ring (e.g., a $C_{3-10}$cycloalkane ring such as cyclohexane ring, a $C_{3-10}$ cycloalkene ring such as cyclohexene ring); a non-aromatic bridged ring (e.g., a bicyclic to tetracyclic bridged hydrocarbon ring such as 5-norbornene ring), and an aromatic ring (e.g., a $C_{6-12}$arene ring such as benzene ring or naphthalene ring, and a condensed ring). These rings may have a substituent (e.g., an alkyl group, a haloalkyl group, a hydroxyl group, an alkoxy group, a carboxyl group, a substituted oxycarbonyl group, an acyl group, an acyloxy group, a nitro group, a cyano group, an amino group, and a halogen atom). The ring comprises an aromatic ring in practical cases.

The preferred catalyst (imide compound) may include the compounds represented by the following formulae (1a) to (1d) and the compound represented by the above formula (4):

[Formula 3]

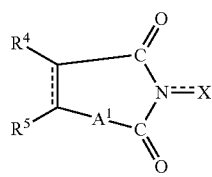
(1a)

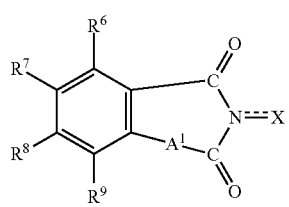
(1b)

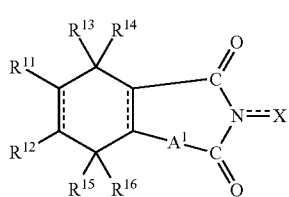
(1c)

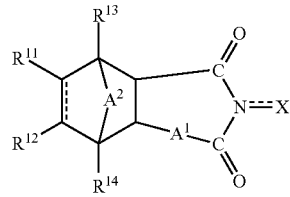
(1d)

wherein -$A^1$- represents a single bond or a group represented by the following formula (A):

[Formula 4]

(A)

$R^4$ to $R^{16}$ are the same or different and each represent a hydrogen atom, an alkyl group as exemplified above, a haloalkyl group, a hydroxyl group, an alkoxy group as exemplified above, a carboxyl group, a substituted oxycarbonyl group as exemplified above, an acyl group as exemplified above, an acyloxy group as exemplified above, a nitro group, a cyano group, an amino group, and a halogen atom as exemplified above; two vicinal groups of $R^6$ to $R^{12}$ (or two groups selected from $R^6$ to $R^{12}$ and attached to adjacent carbon atoms) may bond together to form the same aromatic or non-aromatic ring as described in the above, with the adjacent carbon atoms, or may form a cyclic imino unit represented by the following formula (1e):

[Formula 5]

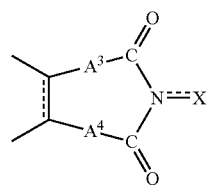
(1e)

(wherein, -$A^3$- and -$A^4$- each represent a single bond or a group represented by the above-mentioned formula (A); provided that when -$A^3$- represents a single bond, -$A^4$- represents a single bond or a group represented by the formula (A), and when -$A^3$- represents a group represented by the formula (A), -$A^4$- represents a single bond.); the aromatic or non-aromatic ring formed by bonding of two vicinal groups of $R^6$ to $R^{12}$ may further has one or two cyclic imino units represented by the formula (1e); in the formula (1d), $A^2$ represents a methylene group or an oxygen atom; and a double line consisting of a solid line and a broken line represents a single bond or a double bond.

Incidentally, the imide compound having a plurality of cyclic imino units may include, for example, compounds represented by the following formulae:

[Formula 6]

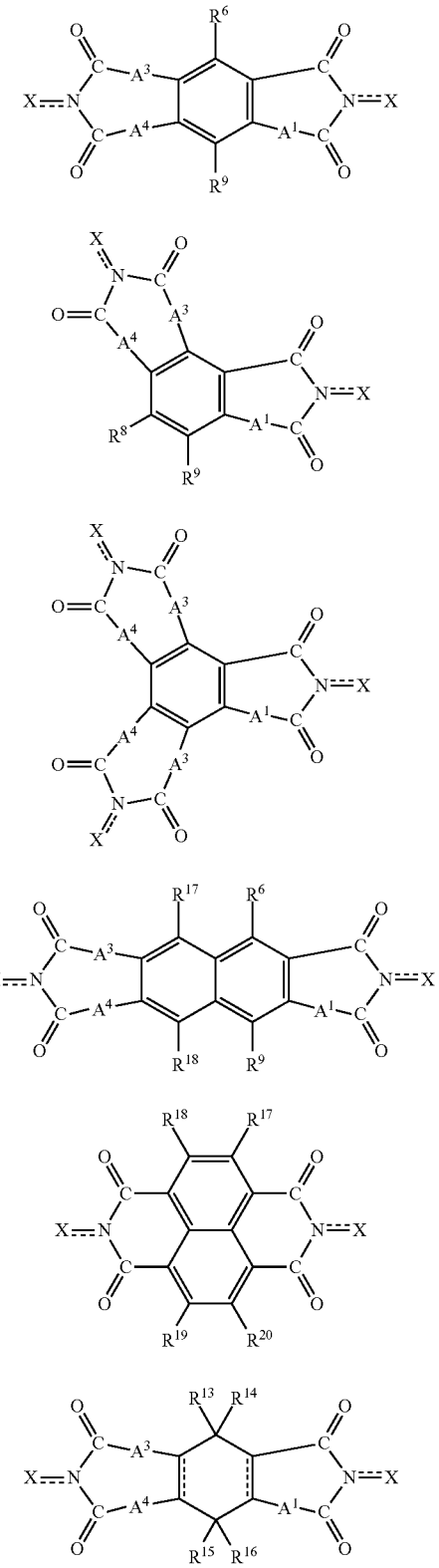

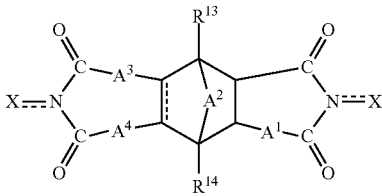

wherein $R^{17}$ to $R^{20}$ are the same or different and each represent a hydrogen atom, an alkyl group as exemplified above, a haloalkyl group, a hydroxyl group, an alkoxy group as exemplified above, a carboxyl group, a substituted oxycarbonyl group as exemplified above, an acyl group as exemplified above, an acyloxy group as exemplified above, a nitro group, a cyano group, an amino group, and a halogen atom as exemplified above; -$A^1$-, $A^2$, -$A^3$-, -$A^4$-, $R^6$, $R^8$, $R^9$, $R^{13}$ to $R^{16}$ and X have the same meanings as defined above; two vicinal groups of $R^6$, $R^7$ to $R^{10}$, and $R^{17}$ to $R^{20}$ may bond together to form the same aromatic or non-aromatic ring as described in the above, with the adjacent carbon atoms; and a double line consisting of a solid line and a broken line represents a single bond or a double bond.

In the substituents $R^4$ to $R^{20}$, the haloalkyl group may include a halo$C_{1-20}$alkyl group such as trifluoromethyl group. Usually the substituents $R^4$ to $R^{20}$ are independently a hydrogen atom, an alkyl group, a carboxyl group, a substituted oxycarbonyl group, a nitro group, or a halogen atom.

Typical examples of the imide compound include a compound in which X is OH group in each of the formulae, for example, N-hydroxysuccinimide or a compound having an acyloxy group (such as acetoxy, propionyloxy, valeryloxy, pentanoyloxy, or lauroyloxy group) or an arylcarbonyloxy group (such as benzoyloxy group) as substituents on α,β-positions of N-hydroxysuccinimide, N-hydroxymaleimide, N-hydroxyhexahydrophthalimide, N,N'-dihydroxycyclohexanetetracarboximide, N-hydroxyphthalimide or a compound having an alkoxycarbonyl group (such as methoxycarbonyl, ethoxycarbonyl, pentyloxycarbonyl, or dodecyloxycarbonyl group) or an aryloxycarbonyl group (such as phenoxycarbonyl group) as a substituent on 4-position and/or 5-position of N-hydroxyphthalimide, N-hydroxytetrabromophthalimide, N-hydroxytetrachlorophthalimide, N-hydroxyhetimide (N-hydroxyhet acid imide), N-hydroxyhimimide (N-hydroxyhimic acid imide), N-hydroxytrimellitimide, N,N'-dihydroxypyromellitimide, an N,N'-dihydroxynaphthalenetetracarboximide (e.g., N,N'-dihydroxynaphthalene-1,8,4,5-tetracarboximide), and 1,3,5-trihydroxyisocyanuric acid; a compound in which X is OR group in the formula (1) (wherein R represents an acyl group such as acetyl group), for example, a compound having an N-acyl skeleton, corresponding to the above-exemplified compound having an N-hydroxy skeleton (i.e., a compound in which X is OH group in the formula (1)) (e.g., N-acetoxysuccinimide, N-acetoxymaleimide, N-acetoxyhexahydrophthalimide, N,N'-diacetoxycyclohexanetetracarboximide, N-acetoxyphthalimide, N-acetoxytetrabromophthalimide, N-acetoxytetrachlorophthalimide, N-acetoxyhetimide (N-acetoxyhet acid imide), N-acetoxyhimimide (N-acetoxyhimic acid imide), N-acetoxytrimellitimide, N,N'-diacetoxypyromellitimide, an N,N'-diacetoxynaphthalenetetracarboximide (e.g., N,N'-diacetoxynaphthalene-1,8,4,5-tetracarboximide), N-valeryloxyphthalimide, and N-lauryloxyphthalimide); a compound corresponding to the above-exemplified compound having an N-hydroxy skeleton (i.e., a compound in which X is OH group in the formula (1)) and being represented by the formula (1) in which X is OR group (wherein R represents a group capable of forming an acetal or hemiacetal group with a hydroxyl group), for example, N-methoxymethyloxyphthalimide, N-(2-methoxyethoxymethyloxy)phthalimide, and N-tetrahydropyranyloxyphthalimide; a compound represented by the formula (1) in which X is OR group (wherein R represents sulfonyl group), for example, N-methanesulfonyloxyphthalimide, and N-(p-toluenesulfonyloxy)phthalimide; a compound represented by the formula (1) in which X is OR group (wherein R represents a residual group obtained by eliminating a hydroxyl group from an inorganic acid), for example, an ester of N-hydroxyphthalimide with sulfuric acid, nitric acid, phosphoric acid, boric acid, and other acids.

The process for producing the catalyst (imide compound) having the cyclic imino unit is described in the above-mentioned Patent Documents 3 to 5 or others, and the catalyst can be produced in accordance with the processes described in these documents. Incidentally, the acid anhydride corresponding to the catalyst may include, for example, a saturated or unsaturated aliphatic dicarboxylic anhydride such as succinic anhydride or maleic anhydride; a saturated or unsaturated non-aromatic cyclic polycarboxylic anhydride (an alicyclic polycarboxylic anhydride) such as tetrahydrophthalic anhydride, hexahydrophthalic anhydride (1,2-cyclohexanedicarboxylic anhydride), 1,2,3,4-cyclohexanetetracarboxylic acid 1,2-anhydride, or methylcyclohexenetricarboxylic anhydride; a bridged cyclic polycarboxylic anhydride (an alicyclic polycarboxylic anhydride) such as het anhydride (het acid anhydride) or himic anhydride (himic acid anhydride); and an aromatic polycarboxylic anhydride such as phthalic anhydride, tetrabromophthalic anhydride, tetrachlorophthalic anhydride, nitrophthalic anhydride, het acid, himic anhydride, trimellitic anhydride, pyromellitic anhydride, mellitic anhydride, 1,8;4,5-naphthalenetetracarboxylic dianhydride, or 2,3;6,7-naphthalenetetracarboxylic dianhydride.

Further, the catalyst (imide compound) also includes a cyclic compound having the skeleton represented by the formula (1) through a linking group or linking skeleton (for example, a biphenyl unit and a bisaryl unit). As the catalyst (imide compound), there may be a compound derived from a tetracarboxybiphenyl compound or an acid anhydride thereof, for example, N,N'-dihydroxybiphenyl tetracarboximide and N,N'-diacetoxybiphenyl tetracarboximide, and in addition, a compound derived from a biphenyl ether tetracarboxylic acid or an acid anhydride thereof (e.g., N,N'-dihydroxybiphenyl ether tetracarboximide and N,N'-diacetoxybiphenyl ether tetracarboximide), a compound derived from a biphenyl sulfone tetracarboxylic acid or an acid anhydride thereof (e.g., N,N'-dihydroxybiphenyl sulfone tetracarboximide and N,N'-diacetoxybiphenyl sulfone tetracarboximide), a compound derived from a biphenyl sulfide tetracarboxylic acid or an acid anhydride thereof (e.g., N,N'-dihydroxybiphenyl sulfide tetracarboximide and N,N'-diacetoxybiphenyl sulfide tetracarboximide), a compound derived from a biphenyl ketone tetracarboxylic acid or an acid anhydride thereof (e.g., N,N'-dihydroxybiphenyl ketone tetracarboximide and N,N'-diacetoxybiphenyl ketone tetracarboximide), a compound derived from a bis(3,4-dicarboxyphenyl)alkane or an acid anhydride thereof (e.g., N,N'-dihydroxybiphenylalkanetetracarboximide and N,N'-diacetoxybiphenylalkanetetracarboximide), and others.

The imide compound represented by the formula (1) may be used alone or in combination. The imide compound may be produced in the reaction system.

In the present invention, the preferred catalyst (the catalyst having the cyclic imino unit or the compound having an N-hydroxy skeleton) includes a water-soluble or water-dispersive imide compound. As the water-soluble or water-dispersive imide compound, there may be an aliphatic dicarboximide, for example, an imide compound (e.g., an alkanedicarboximide and an alkenecarboximide) corresponding to a saturated or unsaturated aliphatic dicarboxylic anhydride such as succinic anhydride or maleic anhydride, and the compound represented by the formula (4) (that is, an isocyanuric acid having an oxygen atom or an —OR group (wherein R has the same meaning as defined above) on at least one nitrogen atom thereof).

The imide compound may be used in the form that the compound is supported on a support (or a carrier) (for example, a porous support such as an activated carbon, a zeolite, a silica, a silica-alumina, or a bentonite). The imide compound is usually employed without being supported on the support in practical cases. For supporting the imide compound on the support, the amount to be supported of the imide compound relative to 100 parts by weight of the support is, for example, about 0.1 to 50 parts by weight, preferably about 0.5 to 30 parts by weight, and more preferably about 1 to 20 parts by weight.

(Transition Metal Co-Catalyst)

The transition metal co-catalyst may also be referred to the Patent Documents 3 to 5, and others. As the transition metal co-catalyst, in practical cases a metal compound having a metal element of the Groups 2 to 15 of the Periodic Table of Elements is used. Incidentally, hereinafter, boron (B) is regarded as a metal element. The metal element may include, for example, an element of the Group 2 (e.g., Mg, Ca, Sr, and Ba), an element of the Group 3 (e.g., Sc, a lanthanoid, and an actinoid), an element of the Group 4 (e.g., Ti, Zr, and Hf), an element of the Group 5 (e.g., V), an element of the Group 6 (e.g., Cr, Mo, and W), an element of the Group 7 (e.g., Mn), an element of the Group 8 (e.g., Fe, Ru, and Os), an element of the Group 9 (e.g., Co, Rh, and Ir), an element of the Group 10 (e.g., Ni, Pd, and Pt), an element of the Group 11 (e.g., Cu), an element of the Group 12 (e.g., Zn), an element of the Group 13 (e.g., B, Al, and In), an element of the Group 14 (e.g., Sn and Pb), and an element of the Group 15 (e.g., Sb and Bi), of the Periodic Table of Elements. Among these metal elements, the transition metal element (the element of the Groups 3 to 12 of the Periodic Table of Elements), particularly, Mn, Co, Zr, Ce, Fe, V. and Mo (among others, Mn, Co, Zr, Ce, and Fe) are preferred. The valence of the metal element is not particularly limited to a specific one, and may be, for example, about 0 to 6.

The metal compound may include an inorganic compound such as a simple substance (or an elemental substance) of the metal element, a hydroxide of the metal element, an oxide of the metal element (including a compound oxide), a halide of the metal element (a fluoride, a chloride, a bromide, and an iodide), a salt of the metal element with an oxo acid (e.g., a nitrate, a sulfate, a phosphate, a borate, and a carbonate), a salt of the metal element with an isopoly acid, or a salt of the metal element with a heteropoly acid; and an organic compound such as a salt of the metal element with an organic acid (e.g., an acetate, a propionate, a cyanate, a naphthenate, and a stearate) or a complex of the metal element. The ligand of the complex may include OH (hydroxo), an alkoxy(e.g., methoxy, ethoxy, propoxy, and butoxy), an acyl (e.g., acetyl and propionyl), an alkoxycarbonyl (e.g., methoxycarbonyl and ethoxycarbonyl), an acetylacetonato, a cyclopentadienyl group, a halogen atom (e.g., chlorine and bromine), CO, CN, oxygen atom, $H_2O$ (aquo), a phosphorus compound such as a phosphine (e.g., a triarylphosphine such as triphenylphosphine), a nitrogen-containing compound such as $NH_3$ (ammine), NO, $NO_2$ (nitro), $NO_3$ (nitrato), ethylenediamine, diethylenetriamine, pyridine, or phenanthroline, and others.

Typical examples of the metal compound may include an inorganic compound such as a hydroxide [e.g., cobalt hydroxide and vanadium hydroxide], an oxide [e.g., cobalt oxide, vanadium oxide, manganese oxide, and zirconium oxide], a halide (e.g., cobalt chloride, cobalt bromide, vanadium chloride, vanadyl chloride, and zirconium chloride), or an salt of an inorganic acid (e.g., cobalt nitrate, cobalt sulfate, cobalt phosphate, vanadium sulfate, vanadyl sulfate, sodium vanadate, manganese sulfate, and zirconium sulfate); a salt of an organic acid [e.g., cobalt acetate, cobalt naphthenate, cobalt stearate, manganese acetate, zirconium acetate, and zirconium hydroxyacetate]; a complex [e.g., a bivalent or tervalent cobalt compound such as cobalt acetylacetonato, a bi- to quinquevalent vanadium compound such as vanadium acetylacetonato or vanadyl acetylacetonato, a bivalent or tervalent manganese compound such as manganese acetylacetonato, and a quadrivalent or quinquevalent zirconium compound such as zirconium acetylacetonato]; and others.

The metal compound may be used alone or in combination. A plurality of metal compounds different in valence may be used in combination.

It is preferable that the transition metal co-catalyst contain at least both of a metal component of the Group 9 of the Periodic Table of Elements (e.g., a cobalt compound) and a metal component of the Group 7 of the Periodic Table of Elements (e.g., a manganese compound). Use of such a combination can improve the catalyst activity of the imide compound.

In combination of a plurality of metal components (or metal compounds), each of the metal components may be used in suitable quantitative proportions as long as the catalyst activity is not inhibited. For example, in a combination use of the metal component of the Group 9 (the cobalt compound) and the metal component of the Group 7 (the manganese compound) of the Periodic Table of Elements, the amount of the metal component of the Group 7 may be, for example, about 0.1 to 5 mol, preferably about 0.5 to 2 mol, and more preferably about 0.7 to 1.5 mol (e.g., about 0.8 to 1.2 mol), in terms of metal elements, relative to 1 mol of the metal component of the Group 9.

Incidentally, the transition metal co-catalyst may be capable of forming a salt with an aromatic carboxylic acid (for example, a dicarboxylic acid and a monocarboxylic acid) produced by the oxidation reaction.

(Other Components)

In the present invention, an organic salt may be used as a co-catalyst. The organic salt comprises a polyatomic cation or polyatomic anion containing an element of the Group 15 (e.g., N, P, As, and Sb) or the Group 16 (e.g., S) of the Periodic Table of Elements bonding to at least one organic group, and a counter ion. Representative examples of the organic salt may include an organic onium salt such as an organic ammonium salt, an organic phosphonium salt, or an organic sulfonium salt. The organic salt may also include a salt of an alkylsulfonic acid; a salt of an arylsulfonic acid which may have a $C_{1-20}$ alkyl group as a substituent; a sulfonate-based ion exchange resin (an ion exchanger); a phosphonate-based ion exchange resin (an ion exchanger); and others. The amount of the organic salt is, for example, about 0.001 to 10 mol, preferably about 0.005 to 5 mol, and more preferably about 0.01 to 3 mol, relative to 1 mol of the imide compound.

In the present invention, a strong acid may be used as a co-catalyst. The strong acid may include, for example, a hydrogen halide, a hydrohalogenic acid, a sulfuric acid, and a heteropoly acid. The amount of the strong acid is, for example, about 0.001 to 3 mol, preferably about 0.005 to 2.5 mol, and more preferably about 0.01 to 2 mol, relative to 1 mol of the imide compound.

In the present invention, further, a carbonyl compound having an electron withdrawing group (such as a fluorine atom or a carboxyl group) may be used as a co-catalyst. The carbonyl compound may include, for example, hexafluoroacetone, trifluoroacetic acid, pentafluorophenyl ketone, and benzoic acid. The amount of the carbonyl compound is, for example, about 0.0001 to 3 mol, preferably about 0.0005 to 2.5 mol, and more preferably about 0.001 to 2 mol, relative to 1 mol of the reaction component (the substrate).

Furthermore, in order to accelerate the reaction, a radical-generating agent or a radical-reaction accelerator or promoter may be present in the system. Such a component may include, for example, a halogen (e.g., chlorine and bromine), a peracid (e.g., peracetic acid and m-chloroperbenzoic acid), a peroxide (e.g., hydrogen peroxide and a hydroperoxide such as t-butylhydroperoxide (TBHP)), nitric acid or nitrous acid or a salt thereof, nitrogen dioxide, and an aldehyde such as benzaldehyde (e.g., an aldehyde corresponding to the aromatic polycarboxylic acid as an object compound). The amount of the component is about 0.001 to 1 mol, preferably about 0.005 to 0.8 mol, and more preferably about 0.01 to 0.5 mol, relative to 1 mol of the imide compound.

(Substrate)

As the aromatic compound having an alkyl group and/or an alkylene group, usually, an aromatic compound in which an alkyl group or an alkylene group (or an alkylidene group) bonds to an aromatic ring (a ring having an aromatic property) may be employed.

It is sufficient to have at least one alkyl or alkylene group in an aromatic hydrocarbon or heterocycle compound in which an alkyl group or an alkylene group (or an alkylidene group) bonds to an aromatic ring (e.g., an aromatic hydrocarbon ring, an aromatic heterocycle). Such a compound may have a plurality of alkyl groups or a plurality of alkylene groups. In addition to the alkyl or alkylene group, the aromatic hydrocarbon or heterocycle compound may have a "lower-order oxidized group" of the alkyl or alkylene group, which is produced by oxidation of these groups and has not yet formed a final carboxyl group or an equivalent thereof (e.g., an acid anhydride group). Thus the oxidizable site of the substrate includes the above-mentioned lower-order oxidized group as well as the alkyl or alkylene group.

Among the aromatic rings, the aromatic hydrocarbon ring may include, for example, a monocyclic or condensed polycyclic hydrocarbon ring corresponding to benzene, naphthalene, acenaphtylene, phenanthrene, anthracene, pyrene, and the like; a ring-assembly hydrocarbon ring, e.g., a hydrocarbon ring corresponding to biphenyl, terphenyl, binaphthyl, and the like; and a bisarene compound in which aromatic hydrocarbon rings are linked through a bivalent group such as an oxygen atom, a sulfur atom, a sulfide group, a carbonyl group, an alkylene group, or a cycloalkylene group, e.g., a bisarene corresponding to biphenyl ether, biphenyl sulfide, biphenyl sulfone, biphenyl ketone, a biphenylalkane, and the like. Moreover, the aromatic heterocycle may include an aromatic heterocycle having about one to three hetero atoms comprising at least one selected independently from the group consisting of an oxygen atom, a sulfur atom, and a nitrogen atom, for example, a thiophene ring, a pyrrole ring, an imidazole ring, an oxazole ring, a thiazole ring, a pyridine ring, a pyridazine ring, a pyrimidine ring, a pyrazine ring, a quinoline ring, an indole ring, an indazole ring, a benzotriazole ring, a quinazoline ring, an acridine ring, and a chromone ring.

Each of these aromatic rings may have a substituent (for example, a carboxyl group, a halogen atom, a hydroxyl group, an alkoxy group, an acyloxy group, a substituted oxycarbonyl group, a substituted or non-substituted amino group, and a nitro group). Moreover, the aromatic ring may be condensed with a non-aromatic ring.

The alkyl group bonding to the aromatic ring may include, for example, a primary or secondary $C_{1-10}$alkyl group such as methyl, ethyl, propyl, isopropyl, butyl, isobutyl, s-butyl, pentyl, isopentyl, hexyl, isohexyl, heptyl, octyl, 2-ethylhexyl, or decyl group. The preferred alkyl group includes a $C_{1-4}$alkyl group, particularly a $C_{1-3}$alkyl group such as methyl group, ethyl group, or isopropyl group. The lower-order oxidized group of the alkyl group may include, for example, a hydroxyalkyl group (e.g., a hydroxy$C_{1-3}$alkyl group such as hydroxymethyl or 1-hydroxyethyl group), a formyl group, a formylalkyl group (e.g., a formyl$C_{1-3}$alkyl group such as formylmethyl or 1-formylethyl group), and an alkyl group having an oxo group (e.g., a $C_{1-4}$acyl group such as acetyl, propionyl, or butyryl group).

Moreover, the alkylene group (or the alkylidene group) bonding to the aromatic ring may include, for example, a secondary $C_{1-10}$alkylene group such as methylene, ethylene, propylene, trimethylene, or butylene group. The preferred alkylene group includes a $C_{1-4}$alkylene group, particularly methylene group as well as a $C_{2-4}$alkylene group (such as ethylene or propylene group), particularly methylene group. The lower-order oxidized group of the alkylene group may include, for example, a hydroxyalkylene group (e.g., a hydroxy$C_{1-3}$alkylene group such as hydroxymethylene or 1-hydroxyethylene group), a carbonyl group, and an alkylene group having an oxo group (e.g., an oxo$C_{1-4}$alkanediyl group such as —$CH_2$—C(═O)— or —$CH_2$—C(═O)—$CH_2$— group).

Incidentally, the alkyl group or the lower-order oxidized group thereof or the alkylene group or the lower-order oxidized group thereof may have a substituent as long as the reaction is not inhibited.

The aromatic compound as the substrate may have a carboxyl group and/or an alkoxycarbonyl group (e.g., a lower alkoxycarbonyl group (e.g., a $C_{1-4}$alkoxy-carbonyl group) such as methoxycarbonyl group or ethoxycarbonyl group) in addition to the alkyl group, the alkylene group, or the lower-order oxidized group thereof.

The aromatic ring may have about 1 to 10 (preferably about 1 to 6 and more preferably about 1 to 4) groups each selected from the alkyl group, the alkylene group, and the lower-order oxidized group, depending on the number of members of the ring. The number of alkylene groups or lower-order oxidized groups thereof is usually about 1 to 3. The aromatic ring preferably has one or two groups each selected from the alkyl group, the alkylene group, and the lower-order oxidized group.

In the aromatic compound having the alkyl group, the number of alkyl groups usually corresponds to the number of carboxyl groups of the aromatic carboxylic acid as an object product.

The aromatic compound having the alkyl group may include, for example, a $C_{6-20}$aromatic hydrocarbon compound having an alkyl group (e.g., a $C_{1-4}$alkyl group such as methyl group) such as toluene, ethylbenzene, propylbenzene, xylene (e.g., o-, m-, or p-xylene), t-butyltoluene (e.g., o-, m-, or p-t-butyltoluene), methylnaphthalene, or methylanthracene; a $C_{6-20}$arene-carboxylic acid having an alkyl group (e.g., a $C_{1-4}$alkyl group such as a methyl group) such as toluic acid (o-, m-, or p-toluic acid) or dimethylbenzoic acid; a $C_{1-4}$alkyl ester of a $C_{6-20}$arene-carboxylic acid having an alkyl group (e.g., a $C_{1-4}$alkyl group such as methyl group) such as methyl toluate (e.g., methyl o-, m-, or p-toluate); and an aromatic compound having an aromatic heterocycle and an alkyl group (e.g., a $C_{1-4}$alkyl group such as methyl group) adjacent to (or bonding to) the aromatic heterocycle, including a heterocycle compound in which an aromatic heterocycle containing one to three hetero atoms selected from the group consisting of an oxygen atom, a sulfur atom, and a nitrogen atom has an alkyl group having about one to six carbon atoms as a substituent, such as 2-methylfuran, 2,5-dimethylfuran, 2-methylthiophene, 2,5-dimethylthiophene, 2-methylpyridine, 3-methylpyridine, 4-methylpyridine, 2,5-dimethylpyridine, 3-ethylpyridine, or 2-methylquinoline.

The aromatic compound having the alkylene group or the lower-order oxidized group thereof may include, for example, dibenzyl, diphenylmethane, benzophenone, and additionally, an aromatic heterocycle compound having an aromatic heterocycle and an alkylene group (e.g., methylene group) adjacent to (or bonding to) the aromatic heterocycle.

The preferred aromatic compound includes an aromatic compound in which an aromatic ring (a ring having an aromatic property, for example, an aromatic hydrocarbon ring) has one or two $C_{1-4}$alkyl and/or $C_{1-4}$alkylene groups as a substituent, and others. In particular, the preferred compound includes a $C_{6-10}$arene having a $C_{1-4}$alkyl group (e.g., toluene and ethylbenzene), particularly an alkylbenzene; and a $C_{1-4}$alkyl ester of a $C_{6-20}$arene-carboxylic acid having a $C_{1-4}$alkyl group (e.g., methyl toluate).

Incidentally, as the substrate, a substrate having a substituent may be used, and the substituent may include various substituents, for example, a halogen atom, an alkyl group, an alkenyl group, an aryl group, a heterocyclic group, an oxo group, a hydroxyl group, an alkoxy group, a hydroxyalkyl group, a carboxyl group, an alkoxycarbonyl group, an acyl group, an amino group, an amino group having a substituent (or a substituted amino group), a cyano group, and a nitro group.

(Oxygen)

As the oxygen which comes in contact with the substrate, any of a molecular oxygen and a nascent oxygen may be used. The molecular oxygen is not particularly limited to a specific one, and may include a pure oxygen or an oxygen diluted with an inactive (or inert) gas (e.g., nitrogen, helium, argon, and carbon dioxide), an air, and a diluted air. Moreover, the oxygen may be generated in the system. The amount of the oxygen is usually not less than 0.5 mol (e.g., not less than 1 mol), preferably about 1 to 10000 mol, and more preferably about 5 to 1000 mol, relative to 1 mol of the substrate. The molar quantity of the oxygen is in excess of the molar quantity of the substrate in practical cases.

(Acid Anhydride)

If necessary, an acid anhydride may be added to the reaction system. The acid anhydride may include, for example, an aliphatic monocarboxylic anhydride such as acetic anhydride, propionic anhydride, butyric anhydride, or isobutyric anhydride; an aromatic monocarboxylic anhydride such as benzoic anhydride; and the acid anhydride as described in the paragraph of the catalyst (e.g., an aliphatic polycarboxylic anhydride, an alicyclic polycarboxylic anhydride, and an aromatic polycarboxylic anhydride). Among these acid anhydrides, an aliphatic monocarboxylic anhydride, particularly an acetic anhydride, is preferred. The amount of the acid anhydride may be, for example, about 0.1 to 100 mol, preferably about 0.5 to 40 mol, and more preferably about 1 to 20 mol, relative to 1 mol of the substrate. A largely excessive amount of the acid anhydride may be used relative to the amount of the substrate.

(Oxidation Reaction)

According to the process of the present invention, the oxygen-oxidation of the substrate (that is, the aromatic compound having the alkyl group and/or the alkylene group) causes an oxygen-oxidation of the alkyl group and/or the alkylene group to produce an oxide corresponding to the substrate; and the oxide includes, for example, a hydroxy compound (e.g., an alkanol having an aromatic ring (e.g., a $C_{6-10}$arylC$_{1-4}$alkanol), such as benzyl alcohol), an aldehyde compound (e.g., an aromatic aldehyde, and an alkanal having an aromatic ring), a ketone compound (e.g., an aryl alkyl ketone such as acetophenone; and an aralkyl alkyl ketone), and an organic acid (e.g., an aromatic carboxylic acid). The hydroxy compound, the aldehyde (formyl) compound and/or the ketone compound are/is further oxygen-oxidized in the reaction system. The oxidation of the hydroxy compound produces a corresponding aldehyde compound, ketone compound, organic acid, and the like, and the oxidation of the aldehyde compound forms a corresponding organic acid. Further, the ketone compound is cleaved by oxidation to produce a corresponding aldehyde (formyl) compound and organic acid. Finally, an aromatic carboxylic acid as an object compound is obtained. Therefore, the hydroxy compound, the aldehyde compound, and the ketone compound, each corresponding to the substrate are sometimes referred to as a reaction intermediate in the oxidation reaction system.

For example, toluene is oxidized to obtain benzoic acid; and ethylbenzene is oxidized to obtain acetophenone and benzoic acid. Moreover, the oxidation of xylene produces toluic acid (by oxidizing one methyl group of xylene) and phthalic acid (or isophthalic acid or terephthalic acid) (by oxidizing two methyl groups of xylene). The oxidation of toluic acid produces phthalic acid (or isophthalic acid or terephthalic acid) (by oxidizing the methyl group of toluic acid); and the oxidation of methyl toluate produces monomethyl phthalate (or monomethyl isophthalate or monomethyl terephthalate) (by oxidizing the methyl group of methyl toluate).

The final reaction product contains the organic acid (e.g., an aromatic carboxylic acid) obtained by the oxidation of the substrate as well as water produced by the reaction. In the process of the present invention, it is assumed that this water is not classified as the reaction solvent.

Incidentally, the carboxyl group produced by the oxidation of the alkyl group or the alkylene group is sometimes decarboxylated in the oxidation reaction system. The reaction route including the decarboxylation produces benzoic acid, for example, by the oxidation of xylene, and methyl benzoate by the oxidation of methyl toluate. When the amount of the decarboxylation product increases, the yield (or amount) of the object organic acid (for example, an aromatic carboxylic acid such as a phthalic acid compound, which is an oxidized product of xylene or methyl toluate) decreases. According to the present invention, use of the imide catalyst can drastically decrease the production of the decarboxylation product as a by-product.

Moreover, in the present invention, since the oxidation reaction is carried out while feeding the imide catalyst, and a substrate, a reaction intermediate and/or a reaction product successively or continuously to the oxidation reaction system, the reaction rate can be improved to produce the aromatic carboxylic acid efficiently. The substrate, the reaction intermediate and/or the reaction product specifically include, for example, at least one member selected from the group consisting of (b-1) an aromatic compound having an alkyl group and/or an alkylene group, as a substrate, (b-2) a carbonyl compound corresponding to the aromatic compound (for example, a reaction intermediate such as a ketone or an aldehyde; and a reaction product such as an aromatic carboxylic acid), and (b-3) water obtainable by the oxidation reaction. Further, probably because the produced aromatic carboxylic acid forms a salt with the transition metal co-catalyst and the salt serves as an active species, the efficiency of the reaction can further be improved. Therefore, the reaction can proceed efficiently even at a small amount of the catalyst and is advantageous in terms of energy and costs. Furthermore, the reaction does not require the use of the reaction solvent (a reaction solvent different from the substrate, the reaction intermediate and the reaction product), and thus can reduce a production loss in a purification step or a complicated operation.

Incidentally, the reaction intermediate and/or the reaction product feeding together with the imide catalyst to the reaction system may be a reaction intermediate and/or a reaction product produced in the reaction system actually; and is usually a separately provided compound corresponding to the reaction intermediate (i.e., the same compound as the reaction intermediate), and/or a separately provided compound corresponding to the reaction product (i.e., the same compound as the reaction product) in practical cases.

(Reaction Operation or Reaction Condition)

In the oxidation reaction, the amount of the catalyst (the imide compound) may be selected from a wide range of about 0.0001 to 100 mol % relative to the reaction component (the substrate; the aromatic compound) in terms of cyclic imino unit, and, for example, be about 0.0005 to 50 mol %, preferably about 0.001 to 30 mol %, and more preferably about 0.005 to 10 mol % in terms of cyclic imino unit, relative to the substrate. Since the present invention can remarkably improve the reaction efficiency, the reaction can proceed efficiently even at a small amount of the imide compound. The amount of the imide compound may be, for example, about 0.0002 to 5 mol %, preferably about 0.0007 to 1 mol %, and more preferably about 0.001 to 0.5 mol %, relative to the substrate. Moreover, the catalyst may be added to the reaction system in a concentration of the catalyst of about 1 to 100,000 ppm, preferably about 5 to 10,000 ppm, and more preferably about 10 to 5,000 ppm in the reaction mixture.

Moreover, the ratio of the imide compound may be selected from the range of about 0.001 to 1000 mol, preferably about 0.05 to 100 mol and more preferably about 0.1 to 10 mol (e.g., about 0.5 to 5 mol) relative to 1 mol of the transition metal co-catalyst (in terms of metal element). Further, the ratio of the catalyst may be at the same level as the ratio of the transition metal co-catalyst or smaller than that of the transition metal co-catalyst. The ratio of the catalyst may be, for example, about 0.01 to 1.1 mol, preferably about 0.02 to 1 mol, and more preferably about 0.03 to 0.9 mol, relative to the 1 mol of the transition metal co-catalyst (in terms of metal element).

As the component to be added to the reaction system together with the catalyst, there may be the substrate (the aromatic compound having the alkyl group and/or the alkylene group), the reaction intermediate (e.g., the hydroxy compound, the ketone, and the aldehyde, each corresponding to the aromatic compound (particularly, the ketone, the aldehyde)) the reaction product (water; and the organic acid such as the aromatic carboxylic acid), and others. These components may be added to the reaction system alone or in combination. Among these components, particularly, the substrate, the ketone, the aldehyde and the aromatic carboxylic acid, each corresponding to the substrate, and/or water are/is practically used. Incidentally, even if the catalyst is added in combination with water, which does not take part in the reaction at all and seems to inhibit the reaction, the reaction rate can be improved remarkably.

The additive component and the catalyst are usually fed in the form of a mixture to the reaction system. The mixture may be in any form, e.g., a solution, a dispersion, and a slurry. The ratio of the additive component fed together with the catalyst to the reaction system may, for example, be about 1 to $1\times10^6$ parts by weight, preferably about 1.5 to $1\times10^5$ parts by weight, more preferably about 2 to $1\times10^3$ parts by weight, and particularly about 3 to 300 parts by weight, relative to 1 part by weight of the catalyst.

A small amount of a solvent may be added to the mixture or reaction system containing the catalyst. The addition of the solvent may uniformly dissolve the catalyst in the reaction system. The solvent may include a halogenated hydrocarbon such as dichloromethane, chloroform, 1,2-dichloroethane, or dichlorobenzene; an aliphatic alcohol such as methanol, ethanol, t-butanol, or t-amyl alcohol; a nitrile such as acetonitrile or benzonitrile; an aliphatic carboxylic acid such as formic acid, acetic acid, propionic acid, butyric acid, isobutyric acid, or hexanoic acid; an ester of an aliphatic carboxylic acid such as ethyl acetate; an amide such as formamide, acetamide, dimethylformamide (DMF), or dimethylacetamide; and others. These solvents may be used as a mixed solvent. Though the solvent is not used preferably, and when the solvent is used, the preferred solvent is a water-soluble organic solvent, for example, a $C_{1-3}$alkanol such as methanol or ethanol; an aliphatic nitrile such as acetonitrile; and an aliphatic $C_{2-4}$-carboxylic acid such as acetic acid. The ratio of the solvent relative to the additive component to be fed together with the catalyst is not more than 80% by weight (e.g., about 0 to 50% by weight), preferably about 0 to 30% by weight (e.g., about 0 to 10% by weight), and more preferably about 0 to 5% by weight (e.g., about 0 to 2% by weight).

The above-mentioned mixture containing the catalyst is fed to the oxidation reaction system successively (intermittently) or continuously. The feeding time of the catalyst (that is, a period of from a beginning of the catalyst addition to an end thereof) may suitably be selected, and may, for example, be about 1 to 10 hours, preferably about 1.5 to 7 hours, and more preferably about 2 to 6 hours. Moreover, the process of the present invention can be applied to a continuous process.

In the oxidation reaction, the components other than the catalyst, for example, the components such as the transition metal co-catalyst, other co-catalysts, and the substrate (the components to be added to the reaction system) may be fed at a time to a reaction vessel in advance of the reaction or at an early (or initial) stage of the reaction; or one or some component(s) may be fed at a time to a reaction vessel in advance of the reaction or at an early stage of the reaction and then the remaining component(s) may be added thereto successively or continuously.

Moreover, the oxygen can be introduced into the reaction system in various forms (or modes) such as a continuous feeding, a successive feeding, and a bulk feeding (or batch feeding), and it is preferable to feed the oxygen to the reaction system continuously. Incidentally, the concentration of the off-gas oxygen from the reaction system is not particularly limited to a specific one, and is, for example, about 0 to 8% by volume, preferably about 0.1 to 7% by volume, and more preferably about 1 to 6% by volume.

To the reaction system may be added the reaction intermediate (e.g., the hydroxy compound, the ketone, and the aldehyde) and/or the reaction product (e.g., the aromatic carboxylic acid) in advance (beforehand or previously). Moreover, when an aromatic compound having an alkyl group and/or an alkylene group, and a carboxyl group protected by a protecting group such as an alkyl group (e.g., an alkoxycarbonyl group), such as methyl toluate is used as the substrate, an aromatic compound corresponding to the aromatic compound and having a free carboxyl group [an aromatic compound having an alkyl group and/or an alkylene group, and a carboxyl group (e.g., toluic acid) (that is, an aromatic carboxylic acid having an alkyl group and/or an alkylene group)] may be added to the reaction system prior to the reaction (or in advance of the reaction). Among these components to be added to the reaction system, an aromatic carboxylic acid (the same aromatic carboxylic acid as the reaction product and/or an aromatic carboxylic acid having an alkyl group and/or an alkylene group) is particularly preferably added to the reaction system prior to the reaction. The ratio of the component to be added to the reaction system prior to the reaction may be, for example, about 0.001 to 15 mol %, preferably about 0.01 to 10 mol %, and more preferably about 0.1 to 7 mol % (particularly, about 1 to 5 mol %) relative to the substrate. In particular, the presence of the aromatic carboxylic acid in the reaction system can significantly improve the reaction rate. The aromatic carboxylic acid may be added to the reaction system at an early stage of the reaction or may be generated in the reaction system during the reaction process of the oxidation reaction.

In the present invention, the oxidation reaction may be carried out in the presence of a small amount of the reaction solvent (e.g., the solvent as exemplified above), and usually, the oxidation reaction is preferably carried out in the absence of the reaction solvent. The amount of the reaction solvent is, for example, not more than 25% by weight (e.g., about 0 to 20% by weight), preferably about 0 to 10% by weight, and more preferably about 0 to 5% by weight (e.g., about 0 to 2% by weight) in the whole reaction phase.

The oxidation reaction produces water in the reaction system, and in order to promote the reaction efficiently, the reaction may be carried out while removing the resulting water from the reaction system (e.g., by distilling off the water). Incidentally, when the water is removed from the reaction system, the removal amount of the water is not particularly limited to a specific one, and preferably, the water is removed from the reaction system in an amount not to cause two-phase separation of the reaction mixture.

Moreover, the removal of the water may be carried out, for example, by a reactive distillation, in which the reaction is conducted with removing the water, by means of a water-separating apparatus (e.g., a decanter), or by a reactive distillation for removing water in combination with a water-separating apparatus (e.g., a decanter). The removal of water during the reaction can promote the oxidation reaction and inhibit the production of a by-product, and therefore, the object reaction product, such as an aromatic carboxylic acid (e.g., an aromatic dicarboxylic acid, and an aromatic monocarboxylic acid) can be obtained with a high yield.

The temperature of the oxidation reaction may be, for example, about 10 to 300° C., preferably about 25 to 250° C., and more preferably about 50 to 200° C., depending on the species of the reactant and that of the substrate, or others. Moreover, the reaction may be carried out at an almost constant temperature. If necessary, the reaction may be carried out at a plurality of temperature zones or with raising or lowering the temperature stepwise or continuously.

The reaction may be carried out under a reduced pressure. Since the solubility of oxygen is higher under a pressurized condition compared with under a reduced pressure, the reaction is usually carried out under an atmospheric pressure or an applied pressure. The reaction pressure may be, for example, about 0.1 to 10 MPa, preferably about 0.12 to 5 MPa, and more preferably about 0.15 to 2 MPa (particularly, about 0.2 to 1 MPa).

The reaction may be conducted by a continuous operation, a batch operation, or a semi-batch operation. After the reaction is completed, the reaction product may be separated and purified by a separation means (e.g., filtration, condensation, distillation, extraction, crystallization, recrystallization, adsorption, and column chromatography) or a combination means thereof.

INDUSTRIAL APPLICABILITY

The aromatic carboxylic acid obtained by the present invention can be used in a variety of fields (e.g., the field of electronic industry materials), for example, a main raw material for a heat-resistant polymer (e.g., a polyimide-series polymer and a polyester-series polymer) and a heat-resistant plasticizer, and a hardening agent for a heat-resistant epoxy resin.

EXAMPLES

Hereinafter, the following examples are intended to describe this invention in further detail and should by no means be interpreted as defining the scope of the invention.

Example 1

Into an air-flow pressure reactor (or air-flow pressurizable reactor) equipped with a dehydrator similar to Dean-Stark apparatus, 300 g (2.8 mol) of p-xylene, 0.20 g (1.1 mmol) of cobalt acetate (bivalent), and 0.20 g (1.2 mmol) of manganese acetate (bivalent) were charged. Nitrogen was introduced into the reactor to raise the reactor pressure to 0.5 MPa. The mixture was heated to 150° C., and the reactor was ventilated with a mixed gas of air and nitrogen to adjust the oxygen concentration contained in off-gas to 5%. A separately prepared mixture of 0.25 g (2.2 mmol) of N-hydroxysuccinimide and 2 g of water was continuously fed in the reactor over 5 hours. Incidentally, it was assumed that the reaction was started at the time the addition of the catalyst was started, and that the reaction was completed at the time the addition of the catalyst was completed. Moreover, the reaction was carried out with trapping the produced water. After the reaction was completed, the reactor was cooled and the pressure was released. The reaction mixture was analyzed by a high-performance liquid chromatography (HPLC) to determine the conversion of the substrate and the amount and yield of the product. The conversion of p-xylene was 35.7%, and 110 g of p-toluic acid (yield 28.9%), 31 g of terephthalic acid (yield 6.68%), and 0.32 g of benzoic acid as a by-product (yield 0.094%) were obtained.

Comparative Example 1

The reaction was conducted in the same manner as in Example 1 except that 2 g of water was used instead of the mixture of N-hydroxysuccinimide and water. The conversion of the substrate and the amount and yield of the product were determined. Incidentally, it was assumed that the reaction was started at the time the addition of the water was started, and that the reaction was completed at the time the addition of the water was completed. As the results of the reaction, the conversion of p-xylene was 1.68%, and 5 g of p-toluic acid (yield 1.31%), 1 g of terephthalic acid (yield 0.22%), and 0.03 g of benzoic acid as a by-product (yield 0.0088%) were obtained.

Example 2

The reaction was conducted in the same manner as in Example 1 except that 0.025 g (0.141 mmol) of trihydroxyisocyanuric acid was used instead of N-hydroxysuccinimide. The conversion of the substrate and the amount and yield of the product were determined. As the results, the conversion of p-xylene was 36.4%, and 113 g of p-toluic acid (yield 29.7%), 21 g of terephthalic acid (yield 4.52%), and 0.30 g of benzoic acid as a by-product (yield 0.0878%) were obtained.

Example 3

The reaction was conducted in the same manner as in Example 1 except that 10 g (73.5 mmol) of p-toluic acid was used in addition to 300 g (2.8 mol) of p-xylene and that the amount of manganese acetate (bivalent) was 0.10 g instead of 0.20 g and the amount of N-hydroxysuccinimide was 0.17 g instead of 0.25 g. The conversion of the substrate and the amount of the product were determined. As the results, the conversion of p-xylene was 48.9%, and the amounts of the products were as follows: 150 g of p-toluic acid, 44 g of terephthalic acid, and 0.40 g of benzoic acid as a by-product.

Comparative Example 2

The reaction was conducted in the same manner as in Example 3 except that 2 g of water was used instead of the mixture of N-hydroxysuccinimide and water. The conversion of the substrate and the amount of the product were determined. Incidentally, it was assumed that the reaction was started at the time the addition of the water was started, and that the reaction was completed at the time the addition of the water was completed. As the results, the conversion of p-xylene was 32.7%, and the amounts of the products were as follows: 90 g of p-toluic acid, 32 g of terephthalic acid, and 0.52 g of benzoic acid as a by-product.

Example 4

The reaction was conducted in the same manner as in Example 3 except that 300 g (2.0 mol) of methyl p-toluate was used instead of 300 g of p-xylene and that the pressure of the reaction system was raised to 0.2 MPa. The conversion of the substrate and the amount of the product were determined. As the results, the conversion of methyl p-toluate was 30%, the amounts of the products were as follows: 110 g of monomethyl terephthalate, 3.5 g of terephthalic acid, and 1 g of methyl benzoate as a by-product. Incidentally, 7 g of p-toluic acid remained in the reaction mixture.

Comparative Example 3

The reaction was conducted in the same manner as in Example 4 except that 2 g of water was used instead of the mixture of N-hydroxysuccinimide and water. The conversion of the substrate and the amount of the product were determined. Incidentally, it was assumed that the reaction was started at the time the addition of the water was started, and that the reaction was completed at the time the addition of the water was completed. As the results of the reaction, the conversion of methyl p-toluate was 16%, and the amounts of the products were as follows: 53 g of monomethyl terephthalate, 2 g of terephthalic acid, and 1.2 g of methyl benzoate as a by-product. Incidentally, 8 g of p-toluic acid remained in the reaction mixture.

Example 5

The reaction was conducted in the same manner as in Example 4 except that a mixture of 0.17 g of N-hydroxysuccinimide and 10 g of methyl p-toluate was used instead of the mixture of N-hydroxysuccinimide and water and that the mixture was continuously fed to the reactor by a slurry pump over 5 hours. The conversion of the substrate and the amount of the product were determined. As the results, the conversion of methyl p-toluate was 28.3%, and the amounts of the products were as follows: 115 g of monomethyl terephthalate, 3.5 g of terephthalic acid, and 1.0 g of methyl benzoate as a by-product. Incidentally, 6 g of p-toluic acid remained in the reaction mixture.

Example 6

The reaction was conducted in the same manner as in Example 5 except that a mixture of 0.017 g of N-hydroxysuccinimide and 10 g of methyl p-toluate was used instead of the mixture of 0.17 g of N-hydroxysuccinimide and 10 g of methyl p-toluate. The conversion of the substrate and the amount of the product were determined. As the results, the conversion of methyl p-toluate was 22.3%, and the amounts of the products were as follows: 88 g of monomethyl terephthalate, 3.5 g of terephthalic acid, and 1.0 g of methyl benzoate as a by-product. Incidentally, 7 g of p-toluic acid remained in the reaction mixture.

Example 7

The reaction was conducted in the same manner as in Example 6 except that 300 g (2.8 mol) of ethylbenzene was used instead of 300 g (2.0 mol) of methyl p-toluate and 10 g of p-toluic acid, that the pressure of the reaction system was raised to 0.4 MPa, and that a mixture of 0.017 g of N-hydroxysuccinimide and 10 g of acetophenone (instead of the mixture of 0.017 g of N-hydroxysuccinimide and 10 g of methyl p-toluate) was continuously fed to the reactor over 1 hour. The conversion of the substrate and the amount of the product were determined. As the results, the conversion of ethylbenzene was 27.0%, and the amounts of the products were as follows: 32 g of acetophenone and 64 g of benzoic acid.

Comparative Example 4

The reaction was conducted in the same manner as in Example 7 except that 10 g of acetophenone (instead of the mixture of 0.017 g of N-hydroxysuccinimide and 10 g of acetophenone) was continuously fed to the reactor. The conversion of the substrate and the amount of the product were determined. Incidentally, it was assumed that the reaction was started at the time the addition of acetophenone was started, and that the reaction was completed at the time the addition of acetophenone was completed. As the results, the conversion of ethylbenzene was 6.74%, the amounts of the products were as follows: 16 g of acetophenone and 16 g of benzoic acid.

The invention claimed is:

1. A process for producing an aromatic carboxylic acid, which comprises oxygen-oxidizing an aromatic compound having an alkyl group and/or an alkylene group as a substrate in the presence of a catalyst and a transition metal co-catalyst to produce the aromatic carboxylic acid corresponding to the aromatic compound, the catalyst comprising a nitrogen atom-containing cyclic compound containing a skeleton represented by the following formula (1) as a constituent element of the cyclic ring:

[Formula 1]

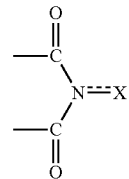

(1)

wherein X represents an oxygen atom or an —OR group (wherein R represents a hydrogen atom or a protecting group for a hydroxyl group), and a double line consisting of a solid line and a broken line and connecting "N" and "X" represents a single bond or a double bond, wherein the oxidation reaction is carried out with feeding a mixture of the catalyst and at least one member selected from the group consisting of a reaction intermediate obtainable by the oxidation reaction of the substrate, and a reaction product obtainable by the oxidation reaction of the substrate successively or continuously to the oxidation reaction system, wherein the oxidation reaction is carried out in the absence of a reaction solvent, and wherein the reaction intermediate and the reaction product comprise at least one member selected from the group consisting of a carbonyl compound corresponding to the aromatic compound, water, and an aromatic carboxylic acid, wherein the mixture comprising the catalyst and at least water among the reaction intermediate and the reaction product is fed to the oxidation reaction system, wherein the water produced by the reaction is not classified as the reaction solvent and the water fed to the oxidation reaction system is separately provided, and wherein the mixture contains the catalyst in an amount of 0.0001 to 0.5 mol % relative to the substrate and is fed to the oxidation reaction system.

2. A production process according to claim 1, wherein the reaction is carried out with removing water produced by the reaction from the reaction system.

3. A production process according to claim 1, wherein the oxidation reaction is carried out with feeding a mixture of (a) the catalyst and at least one member selected from the group consisting of the following components (b-2) and (b-3) successively or continuously to the oxidation reaction system:

(b-2) a carbonyl compound corresponding to the aromatic compound, and (b-3) water, wherein the carbonyl compound is at least one member selected from the group consisting of an aldehyde compound and a ketone compound, and wherein the feeding mixture comprises the catalyst and at least (b-3) water.

4. A production process according to claim 1, wherein the catalyst comprises a water-soluble or water-dispersive imide compound, the substrate comprises an aromatic compound having one or two $C_{1-4}$alkyl and/or $C_{1-4}$alkylene substituent(s) on an aromatic ring thereof, and the aromatic carboxylic acid produced by the oxidation reaction is capable of forming a salt with the transition metal co-catalyst.

5. A production process according to claim 1, wherein the catalyst comprises at least one member selected from the group consisting of an alkanedicarboximide, an alkenecarboximide, and an isocyanuric acid having an oxygen atom or an —OR group on at least one nitrogen atom thereof, wherein R has the same meaning as defined in claim 1.

6. A production process according to claim 1, wherein the transition metal co-catalyst at least contains a metal component of the Group 9 of the Periodic Table of Elements and a metal component of the Group 7 of the Periodic Table of Elements.

7. A production process according to claim 1, wherein the transition metal co-catalyst contains a cobalt compound and a manganese compound.

8. A production process according to claim 1, wherein the ratio of the reaction intermediate and the reaction product is about 1 to 300 parts by weight relative to 1 part by weight of the imide catalyst.

* * * * *